(12) United States Patent
Sano

(10) Patent No.: US 6,309,103 B1
(45) Date of Patent: Oct. 30, 2001

(54) X-RAY IMAGE APPARATUS HAVING CALCULATING MEANS FOR CALCULATING THE OBSERVING AREA IN THE SUBJECT

(75) Inventor: Takayuki Sano, Takatsuki (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/371,277

(22) Filed: Aug. 10, 1999

(30) Foreign Application Priority Data

Aug. 31, 1998 (JP) .................................................. 10-245679

(51) Int. Cl.$^7$ ....................................................... A61B 6/04
(52) U.S. Cl. .............................. 378/205; 378/20; 378/195
(58) Field of Search ............................. 378/20, 193, 195, 378/196, 197, 198, 205, 208

(56) References Cited

U.S. PATENT DOCUMENTS

| | | | |
|---|---|---|---|
| 4,829,986 | * 5/1989 | Eichler et al. | 601/4 |
| 4,872,193 | * 10/1989 | Elff et al. | 378/196 |
| 5,090,401 | * 2/1992 | Schwieker | 601/4 |
| 5,285,772 | * 2/1994 | Rattner | 601/4 |
| 5,395,299 | * 3/1995 | Herrmann et al. | 601/2 |
| 5,542,906 | * 8/1996 | Herrmann et al. | 601/2 |
| 5,583,901 | * 12/1996 | Reitter et al. | 378/4 |

* cited by examiner

Primary Examiner—Robert H. Kim
Assistant Examiner—Allen C Ho
(74) Attorney, Agent, or Firm—Kanesaka & Takeuchi

(57) ABSTRACT

An X-ray image apparatus is formed of an X-ray irradiation device for irradiating X-ray to a subject with an observing area, and an X-ray image taking device for receiving the X-ray irradiated from the X-ray irradiation device and passing through the subject. The X-ray image taking device provides image signals of the X-ray passing through the subject. A support device is connected to the X-ray irradiation device and the X-ray image taking device for supporting and moving both devices around the subject. A calculating device is electrically connected to the X-ray image taking device for calculating a location of the observing area in the subject by image signals obtained from at least two different directions. The center of rotation for the X-ray irradiation device and the X-ray image taking device is adjusted to be the center of the observing area to thereby easily read the images from different directions.

5 Claims, 2 Drawing Sheets

X-RAY IMAGE APPARATUS HAVING CALCULATING MEANS FOR CALCULATING THE OBSERVING AREA IN THE SUBJECT

BACKGROUND OF THE INVENTION AND RELATED ART STATEMENT

The invention relates to an X-ray image apparatus for conducting fluoroscopy or radiograph by X-ray, especially an improvement of the X-ray image apparatus for conducting fluoroscopy or radiograph from various directions while allowing the apparatus to rotate around an examinee or subject to be examined.

There is known an X-ray image apparatus, which is a combination of an X-ray tube and an image intensifying TV camera, for conducting fluoroscopy or radiograph for an examinee to mainly medically examine the examinee. The X-ray image apparatus may be rotated around the examinee to conduct fluoroscopy or radiograph from various directions. In this case, if the center of rotation of the X-ray apparatus does not coincide with an observing area to be examined, the locations of the observing area shown in the different images taken from the various directions become different to make observation of the images difficult.

Therefore, it is required to adjust the height and so on of an examination table on an examination base to allow the observing area to coincide with the center of rotation of the X-ray apparatus. Conventionally, an operator considers a location of the observing area based on a knowledge of anatomy and experiences, and manually adjusts so that the center of rotation of the X-ray apparatus coincides with the location of the observing area.

However, even if the operator is a skilled person, it is very difficult to estimate the location of the observing area in a body of the examinee. Practically, the observing area can not be located in the center of the image. Therefore, conventionally, the location is roughly set, and the filming or observing range is set greater than the actual observing area. As a result, an X-ray is irradiated to unnecessary portions, which may cause excess amount of exposure to the X-ray.

The present invention has been made in view of the above problems, and an object of the invention is to provide an X-ray image apparatus, which can correctly take the position of a subject to be observed.

Another object of the invention is to provide an X-ray image apparatus as stated above, wherein the center of rotation of the X-ray apparatus can be set easily according to the position of the subject.

Further objects and advantages of the invention will be apparent from the following description of the invention.

SUMMARY OF THE INVENTION

In order to attain the above objects, an X-ray image apparatus of the invention comprises X-ray irradiation means for irradiating X-ray to a subject, i.e. patient, with an observing area; X-ray image taking means for receiving the X-ray irradiated from the X-ray irradiation means and passing through the subject, the X-ray image taking means providing image signals for the X-ray passing through the subject; support means connected to the X-ray irradiation means and the X-ray image taking means for supporting and moving both means around the subject, and calculating means for calculating a location of the observing area in the subject by image signals obtained from at least two different directions.

Also, the X-ray image apparatus may include control means for controlling a relative position of the support means with respect to the subject in order to accord the center of rotation of the support means with the observing area in the subject based on the information of the location of the observing area by the calculating means.

Further, the X-ray image apparatus may include display means for displaying the locational information of the calculated observing area.

In case two X-ray images different in directions are taken, it is possible to calculate the location of the observing area relative to the center of rotation when the X-ray irradiation means and the X-ray image taking means are rotated through the support means. Namely, since the observing area is shown in each X-ray image, the location of the observing area in each image can be obtained. On the other hand, since the rotational angles when the two X-ray images are taken are known, it is possible to calculate the location of the observing area relative to the center of the rotation by the locations of the observing areas in the images and the rotational angles.

Since the location of the observing area relative to the center of the rotation is calculated, the control means for controlling the relative position of the support means with respect to the subject may be actuated based on the calculation to automatically control such that the observing area in the subject coincides with the center of rotation. Also, the locational information of the observing area may be displayed, by which the locational adjustment may be made such that the observing area in the subject coincides with the center of the rotation manually. In case of the automatic locational adjustment, since the work of an operator is eliminated, it is very convenient. In case of the manual locational adjustment, since the location of the observing area has been obtained accurately, the locational adjustment to accord the observing area with the center of the rotation can be made accurately.

DETAILED DESCRIPTION OF PREFERRED EMBODIMENTS

The actual embodiment of the invention will be explained in detail with reference to the drawings.

Figure 1:
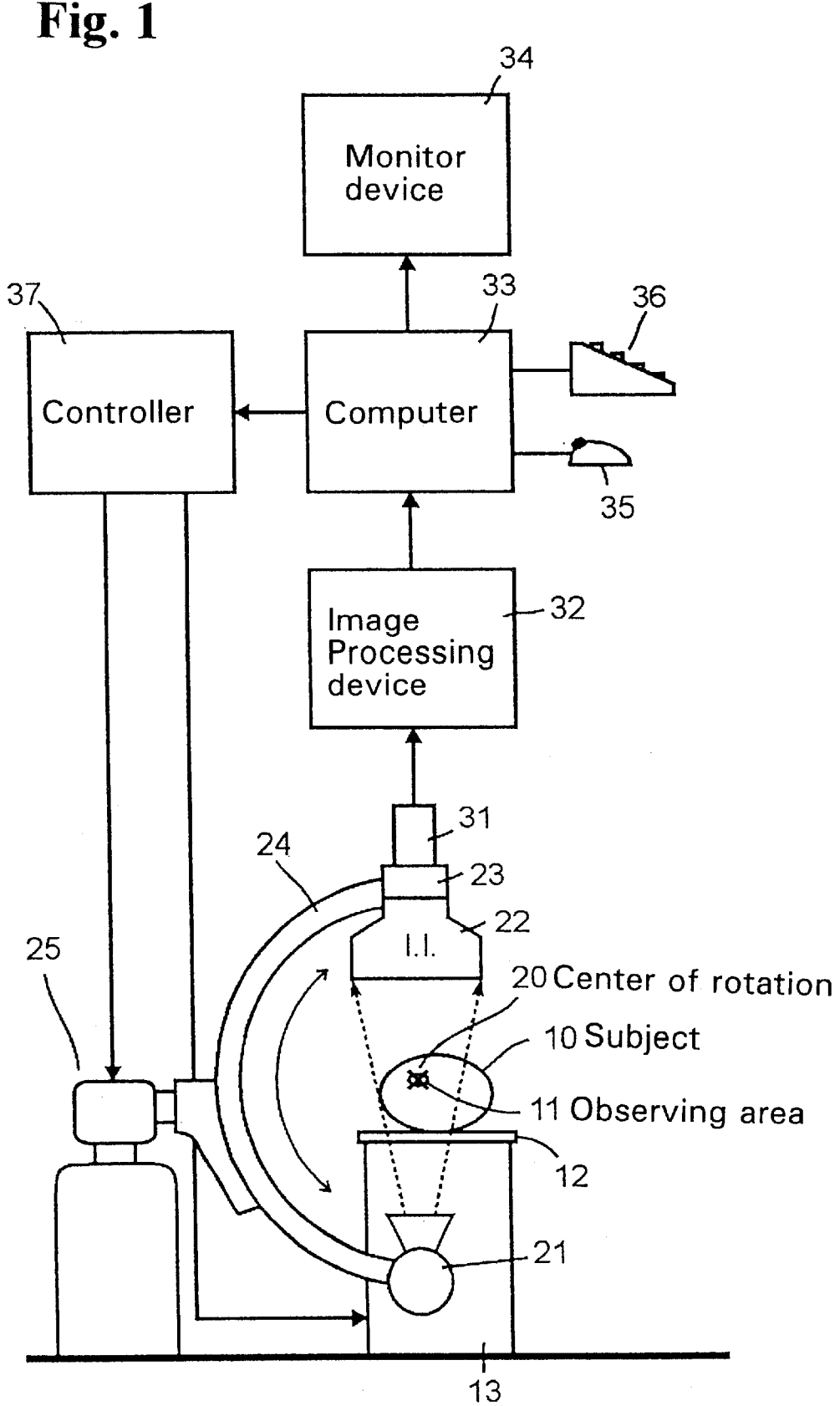
FIG. 1 is a block diagram for showing an actual embodiment of the invention.

In FIG. 1, a subject or examinee 10 to be observed is placed on an examination table 12 on an examination base 13, to which X-ray is irradiated from an X-ray tube 21. The X-ray tube is attached to one end of a C-shape arm 24, and attached to the other end thereof are an image intensifier (I.I.) 22, a TV camera 31 and an optical system 23 between the image intensifier 22 and TV camera 31. These devices are attached to the ends of the C-shape arm 24 such that the X-ray tube 21 faces the image intensifier 22, optical system 23 and TV camera 31 with the subject 10 interposed therebetween.

The C-shape arm 24 is supported by a support device 25, and is arranged to be rotated as shown by an arrow along an arc of the C-shape arm 24, i.e. around a center 20 of rotation. Further, the support device 25 is formed such that the horizontal and vertical positions and an angle of a rotational face of the C-shape arm 24 can be changed. The examination base 13 is formed such that the height, i.e. vertical position, of the examination table 12 can be changed. The positions of the support device 25 and the examination base 13 are controlled based on the order from a controller 37.

X-ray irradiated from the X-ray tube 21 to the object 10 passes through the object 10 and enters into the image intensifier 22, wherein a brightness of the image of the passed X-ray is intensified and the optical image is outputted. The optical image is lead to the TV camera 31 through the optical system 23 to thereby obtain video signals of the X-ray image. The video signals are transmitted to an image monitor device 34 through an image processing device 32 and a computer 33. The X-ray image of the subject 10 is displayed in the image monitor device 34.

Now, it is assumed that an object or observing area 11 of the examinee to be observed exists in the subject 10, and is observed from various directions. The location of the object 11 can not be seen from the outside by naked eyes, but the object 11 can be displayed as the X-ray image. Therefore, the location of the object is recognized through the X-ray image. Thus, before the X-ray images are obtained actually from the various directions, the X-ray images from the proper two directions are obtained beforehand.

Figure 2:
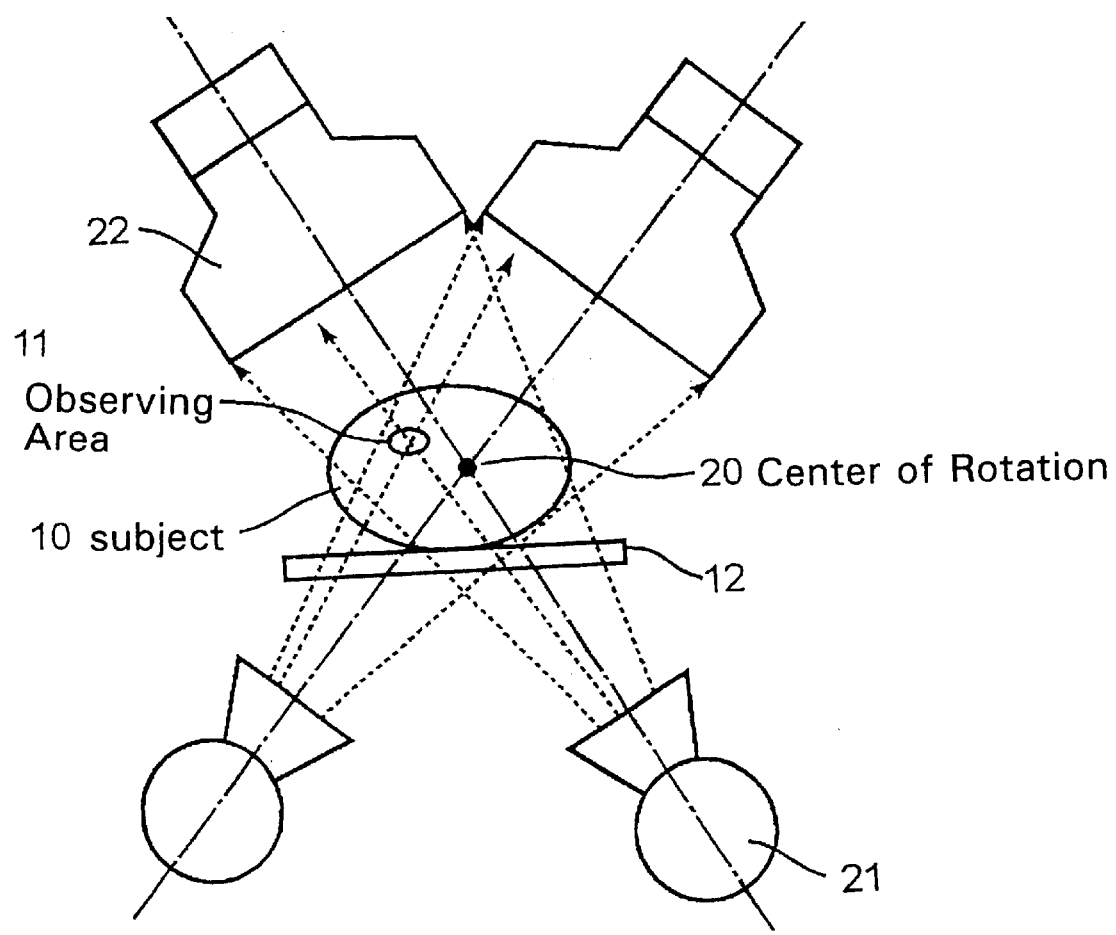
FIG. 2 is a diagram for explaining an operation thereof.

As shown in FIG. 2, in the X-ray images from the different angles, the center 20 of rotation is always projected to the center of an incident plane of the image intensifier 22, but the projected positions of the object 11 become different. Thus, in view of the projected positions of the object 11 in the two images from the different directions, it is possible to obtain a position of the object 11 relative to the center 20 of the rotation.

Actually, the X-ray images from the two directions are displayed in the image monitor device 34, and the location of the object 11 is designated in the displayed image by using a mouse 35 or key board 36 connected to the computer 33. Accordingly, the location of the object 11 is inputted through the images from the two different directions. The computer 33 calculates the location of the object 11 relative to the center 20 of the rotation by the inputted locational information and the angular information when the two images are obtained.

The calculated result is transmitted to the controller 37 to output an order to the support device 25 and the examination table 13 to thereby control the same. As a result, the height of the examination table 12 is adjusted, the horizontal and vertical positions of the C-shape arm 24 supported by the support device 25 are adjusted and so on, so that the center 20 of the rotation of the C-shape arm 24 is automatically set to correspond to the object 11 in the subject or examinee 10.

After this kind of locational adjustment is done, an actual observation for the subject 10 is made from the various directions. Such observation includes fluoroscopy displaying an X-ray image on the image monitor device 34, and an X-ray filming or radiograph for recording image signals after image processing by a recording device (not shown). Since the center 20 of the rotation of the C-shape arm 24 corresponds to the object 11, the images of the object 11 in the X-ray images from all the directions are located in the center of the screen or film. There is no situation such that the image of the object 11 moves in the screen when the C-shape arm 24 is rotated. Namely, when the C-shape arm 24 is rotated, the image of the object 11 is always located in the center of the screen while the observation direction is simply changed. Thus, the object 11 to be observed is not lost in the screen, and the observation can be made easily. Further, since the image of the object 11 is always located in the center of the screen, an X-ray irradiation range can be set to the minimum corresponding to the size of the object 11, Therefore, it is possible to reduce the X-ray exposing amount by deleting the X-ray irradiation to an unnecessary portion.

In the above embodiment, after a relative position of the object 11 relative to the center 20 of the rotation is obtained, the controller 37 controls automatically such that the object 11 coincides with the center 20 of the rotation. However, the location may be adjusted or controlled manually, not automatically. In this case, it is formed such that the requested information about the relative position of the object 11 to the center 20 of the rotation is displayed on a screen. An operator watches the information and operates manually the support device 25 and the examination base 13 to adjust the location. In this case, the object 11 is designated on the images of the X-ray screen obtained from the two directions, and the location is calculated. Therefore, the location of the object 11 is obtained precisely. It is also possible to set the precise location though the manual operation is slightly cumbersome.

In addition, the actual structure may be changed in different ways without changing the subject of the invention. For example, the support device 25 for supporting the X-ray tube 21, image intensifier 22 and so on need not have the C-shape arm 24, it may have a structure such that the X-ray tube 21, image intensifier 22 and so on are rotated to change the directions of fluoroscopy and radiograph.

As explained above, in the X-ray image apparatus of the invention, it is possible to obtain the location of the object to be observed accurately, and to set the center of the rotation corresponding to the location of the object. Therefore, the object is always located in the center of the screen or film in fluoroscopy and radiograph from any directions. Thus, the observation can be made easily, and also, it is possible to reduce the amount of irradiation by setting the irradiation range of X-ray to the minimum.

While the invention has been explained with reference to the specific embodiments of the invention, the explanation is illustrative and the invention is limited only by the appended claims.

What is claimed is:

1. An X-ray image apparatus, comprising:
    X-ray irradiation means for irradiating X-ray to a subject with an observing area,
    X-ray image taking means for receiving the X-ray irradiated from the X-ray irradiation means and passing through the subject, said X-ray image taking means providing image signals by the X-ray passing through the subject,
    support means connected to the X-ray irradiation means and the X-ray image taking means, said supporting means supporting and moving both means around the subject,
    calculating means electrically connected to the X-ray image taking means for calculating a location of the observing area in the subject by image signals obtained from at least two different directions, said calculating means, in setting the observing area, receiving at least two images of the subject with the observing area different in directions without setting a center of rotation of the support means for the observing area, and calculating the location of the observing area with respect to the center of the rotation, said center being located in a middle of a line connecting between the X-ray irradiation means and the X-ray image taking means, and control means electrically connected to the calculating means for controlling a relative position of the support means with respect to the subject, said control means, upon receiving the location of the observing area with respect to the center of rotation, moving the support means to accord the center of rotation of the support means with the observing area in the subject.

2. An X-ray image apparatus according to claim 1, further comprising a display connected to the calculating means for showing the image of the subject taken by the X-ray image taking means, and means for indicating the observing area in the display, said calculating means, upon receiving information of the observing area from the means for indicating the observing area, calculating the location of the observing area with respect to the center of the rotation.

3. An X-ray image apparatus according to claim 2, further comprising an examination table for allowing the subject to be placed, said control means being connected to the examination table and the support means for moving the examination table and the support means independently so that the observing area is set in said center.

4. An X-ray image apparatus according to claim 3, wherein said calculating means obtains differences of locations between the observing areas in the at least two different images and angles between the at least two different images, and calculates a location of the observing area.

5. An X-ray image apparatus according to claim 4, wherein said support means is rotatable around the subject with respect to said center.

* * * * *